(12) United States Patent
Futatsugi et al.

(10) Patent No.: US 6,572,537 B2
(45) Date of Patent: Jun. 3, 2003

(54) ENDOSCOPE APPARATUS

(75) Inventors: Yasuyuki Futatsugi, Hachioji (JP); Hidetoshi Saito, Hanno (JP); Yosuke Yoshimoto, Hachioji (JP); Susumu Aono, Hachioji (JP); Satoshi Honma, Hino (JP); Hitoshi Karasawa, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 338 days.

(21) Appl. No.: 09/769,073

(22) Filed: Jan. 25, 2001

(65) Prior Publication Data

US 2001/0016679 A1 Aug. 23, 2001

(30) Foreign Application Priority Data

Feb. 2, 2000 (JP) ........................ 2000-025566

(51) Int. Cl.[7] .................................................. A61B 1/00
(52) U.S. Cl. ...................................................... 600/133
(58) Field of Search ........................ 128/6, 4; 600/133, 600/127, 176; 606/47; 356/241

(56) References Cited

U.S. PATENT DOCUMENTS 4,491,865 A    1/1985   Danna et al.
4,993,405 A  * 2/1991   Takamura et al. ............. 128/6

FOREIGN PATENT DOCUMENTS

| DE | 3740416 A1 | 6/1989 | |
| JP | 10-234649 | 9/1998 | |
| JP | 2001053989 | * 2/2001 | .......... H04N/5/225 |

* cited by examiner

Primary Examiner—Henry Bennett
Assistant Examiner—Sabrina Dagostino
(74) Attorney, Agent, or Firm—Scully, Scott, Murphy & Presser

(57) ABSTRACT

An endoscope includes an image pickup unit 30 having a solid-state image pickup device 32 such as a CCD on a tip end side of an elongate insertion section. This image pickup unit 30 constitutes a tip end side unit 36U and a rear end side unit 43U by conducting a surface treatment (metallization) to nonmetal members such as a tip end cover glass 31 and a rear end cover glass 35, and by airtight coupling surface-treated portions of the nonmetal members to metal members such as a tip end cover glass frame 36 and a rear end cover glass frame 43 by brazing using soldering, and constitutes an optical system unit 60 by airtight coupling the metal members to metal members of an insulating unit 38U formed by airtight coupling a pipe member 41 and a ring member 42 to an insulating frame 38 by welding.

24 Claims, 6 Drawing Sheets

ENDOSCOPE APPARATUS

This application claims benefit of Japanese Application No. 2000-25566 filed in Japan on Feb. 2, 2000, the content of which are incorporated by this reference.

BACKGROUND OF THE INVENTION

1. Field of the Invention

The present invention relates to an improved endoscope capable of being successfully subjected to autoclave sterilization (high-pressure, high-temperature steam sterilization).

2. Description of the Related Art

At present, endoscopes are widely employed. An endoscope can observe a deep region and the like within a body cavity or the like by inserting an elongate insertion portion into the body cavity, and can conduct a therapeutic treatment by using a treatment tool at need. To prevent infectious disease and the like, it is essential to disinfect and sterilize a medical endoscope of this type.

Conventional disinfection and sterilization treatments have mainly been a gaseous sterilization treatment employing sterilization gas such as ethylene oxide gas and a sterilization treatment with a disinfectant. However, as is well known, sterilization gas is deadly poison and every country increasingly restricts use of the sterilization gas so as to prevent environmental pollution.

Further, aeration is carried out in the course of the gas sterilization treatment stated above. This aeration is intended to remove gas adhering to a sterilized equipment after sterilization. Since the aeration takes a lot of time, the sterilized endoscope cannot be disadvantageously used right after the sterilization. Besides, the gas sterilization treatment as stated above disadvantageously requires high running cost.

Meanwhile, the sterilization treatment with a disinfectant has a disadvantage in that the management of the disinfectant is complicated. Further, the sterilization treatment with a disinfectant requires a large cost for the disposal of the used disinfectant.

In these circumstances, therefore, autoclave sterilization (high-pressure, high-temperature steam sterilization) becomes popular as the sterilization of endoscope equipment. The autoclave sterilization (high-pressure, high-temperature steam sterilization) does not follow complicated operation, allows an endoscope to be used soon after the sterilization and requires low running cost.

Typical conditions for the autoclave sterilization are specified by the American National Standard Institute authorized, US standard ANSI/AAMI ST37-1992 published by the Medical Equipment Development Association. According to this condition, a sterilization step for pre-vacuum type sterilization is conducted at 132° C. for 4 minutes, and a sterilization step for gravity type sterilization is conducted at 132° C. for 10 minutes.

However, high-pressure, high-temperature steam used for the autoclave sterilization has a property of transmitting a polymeric material such as rubber or plastic which constitutes the endoscope equipment, an adhesive agent and the like. Epoxy resin which has been conventionally, normally used as an adhesive agent, in particular, tends to be deteriorated by high-temperature steam and to peel off. Due to this, if autoclave sterilization is conducted, there is fear that steam easily enters the interior of a lens system.

Furthermore, due to the difference in the coefficient of thermal expansion among materials, a stress is applied to respective members constituting the endoscope equipment. This stress causes the adhesive agent used between the respective members to peel off, with the result that steam may possibly enter the interior of the lens system.

According to the conventional endoscope, therefore, if the endoscope is placed into an autoclave sterilization apparatus and subjected to autoclave sterilization, steam enters even the interior of the structure which has been constituted watertight by an ordinary method using an O ring, an adhesive agent or the like.

Moreover, a vacuum step is conducted prior to a sterilization step in the course of the autoclave sterilization. In this connection, there is proposed a method of placing an endoscope into an autoclave sterilization apparatus while the interior and exterior of the apparatus are kept continuous to each other at the time of this vacuum step prior to the sterilization step. This method is intended to prevent an envelope tube used at the bent portion of the insertion portion of the endoscope from rupturing. According to this method, steam for the autoclave sterilization is positively infiltrated into the endoscope.

If an endoscope having an object lens fixed thereto by an adhesive agent is subjected to autoclave sterilization, for example, steam is infiltrated into the interior of an object optical system through the adhesive agent.

If an endoscope having an object lens fixed thereto by an adhesive agent is placed into an autoclave sterilization apparatus and subjected to autoclave sterilization, steam is infiltrated even into the interior of the object optical system through the adhesive agent. As a result, if the endoscope is taken out from the autoclave sterilization apparatus into a room after the autoclave sterilization and observed from the eyepiece of the endoscope, then the lens becomes clouded up with steam and appears foggy. This fog is gradually cleared off and a normal observation image can be obtained.

Nevertheless, while the lens is clouded as stated above, the endoscope cannot be used. Due to this, a test using the endoscope makes little progress, which is considerably inconvenient.

Additionally, autoclave sterilization is sometimes repeatedly conducted or continuously conducted for a long time. In this case, the junctions of the object optical system are greatly deteriorated by the high-pressure, high-temperature steam used for the autoclave sterilization. The junction regions of components made of a stainless material constituting the object optical system may possibly peel off.

The above-stated phenomena also occur to an electronic endoscope including a solid-state image pickup device such as a CCD. The electronic endoscope is comprised of an image pickup unit including an object optical system arranged on the image incidence end face of the solid-state image pickup device. The constituent components made of a stainless material of the image pickup unit including the object optical system are coupled to one another by an ordinary adhesive agent.

If the electronic endoscope as stated above is placed into an autoclave sterilization apparatus and subjected to autoclave sterilization, high-pressure, high-temperature steam used for this autoclave sterilization enters the interior of the image pickup unit including the object optical system. Due to this, if an endoscope image picked up by the image pickup unit is displayed on a monitor, a normal image cannot be shown thereon because of the cloud or the like of the object lens within the image pickup unit. Further, if autoclave sterilization is conducted repeatedly or conducted continuously for a long time, the junctions of the respective constituent components of the image pickup unit may possibly peel off.

To solve the above-stated disadvantages, there is proposed an endoscope described in, for example, Japanese Patent Application No. 10-234649 filed previously by the applicant of the present application which endoscope is provided with an airtight unit having optical elements and insulating members airtight coupled to a metal frame by soldering. The airtight unit is capable of preventing the entry of steam from the outside of the endoscope into the optical system.

The above-stated airtight unit includes a solid-state image pickup device such as a CCD and electronic components such as an IC. In the airtight unit, these components are coupled by an adhesive agent at the time of assembling an optical member such as a lens, an image pickup unit and the like.

The above-stated endoscope, however, has a disadvantage in that if the image pickup unit is small in size, heat is transferred to the image pickup device such as a CCD and the electronic components such as an IC during a soldering operation when the image pickup unit is assembled, and the electronic components may be possibly damaged or the adhesive agent may possibly peel off.

OBJECT AND SUMMARY OF THE INVENTION

It is an object of the present invention to provide an endoscope capable of ensuring airtight coupling and constituting an optical system unit which electronic components and the like are unlikely to be damaged.

It is another object of the present invention to provide an endoscope capable of preventing optical members such as an object lens and a cover glass from being deteriorated by high-pressure, high-temperature steam used for autoclave sterilization, preventing the optical members from becoming clouded up with dew generated by the entry of steam and being subjected to autoclave sterilization repeatedly.

It is yet another object of the present invention to provide an endoscope capable of preventing the formation of dew (or becoming clouded) within a cover glass even if the endoscope is quickly cooled down after the autoclave sterilization.

It is yet another object of the present invention to provide an endoscope capable of easily adjusting a distance (focusing) between a lens group and a solid-state image pickup device and being observed by a clear endoscope image.

It is yet another object of the present invention to provide an endoscope capable of making the outside diameter of the periphery of the lens of an image pickup unit, reducing the outside diameter of an insertion section and easing patients' burden.

An endoscope according to the present invention comprises an optical system unit having a plurality of units formed by airtight coupling a metal member to at least a part of the surface of a nonmetal member which surface has been metallized by soldering or brazing, and formed integrally by airtight welding the metal members of the plurality of units.

Other characteristics and advantages of the present invention will become fully obvious on reading the following description.

DETAILED DESCRIPTION OF THE PREFERRED EMBODIMENTS

The embodiments of the present invention will be described hereinafter with reference to the accompanying drawings.

[First Embodiment]

Figure 1:
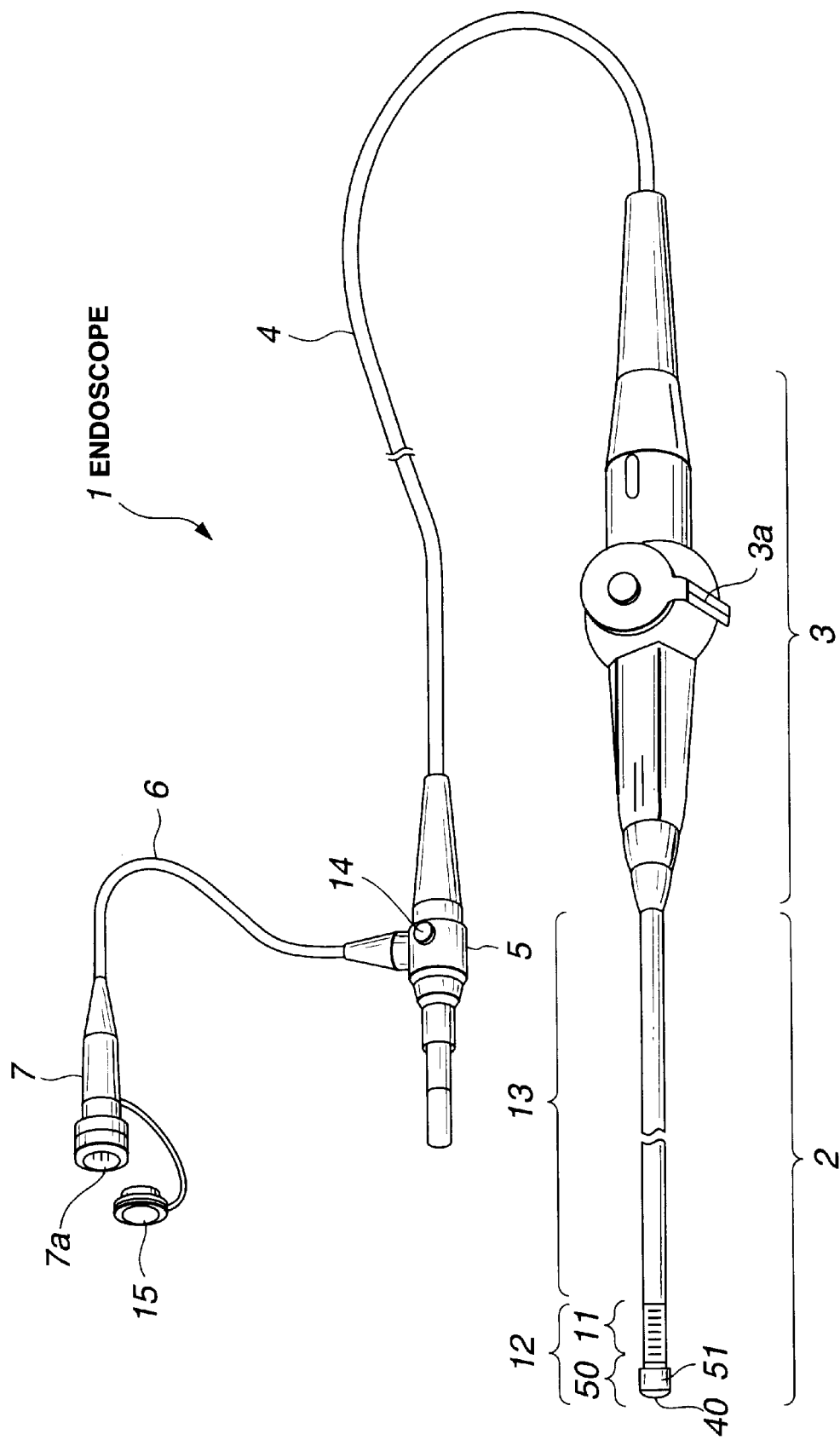
FIG. 1 is an outside view showing an endoscope in the first embodiment according to the present invention.
Figure 2:
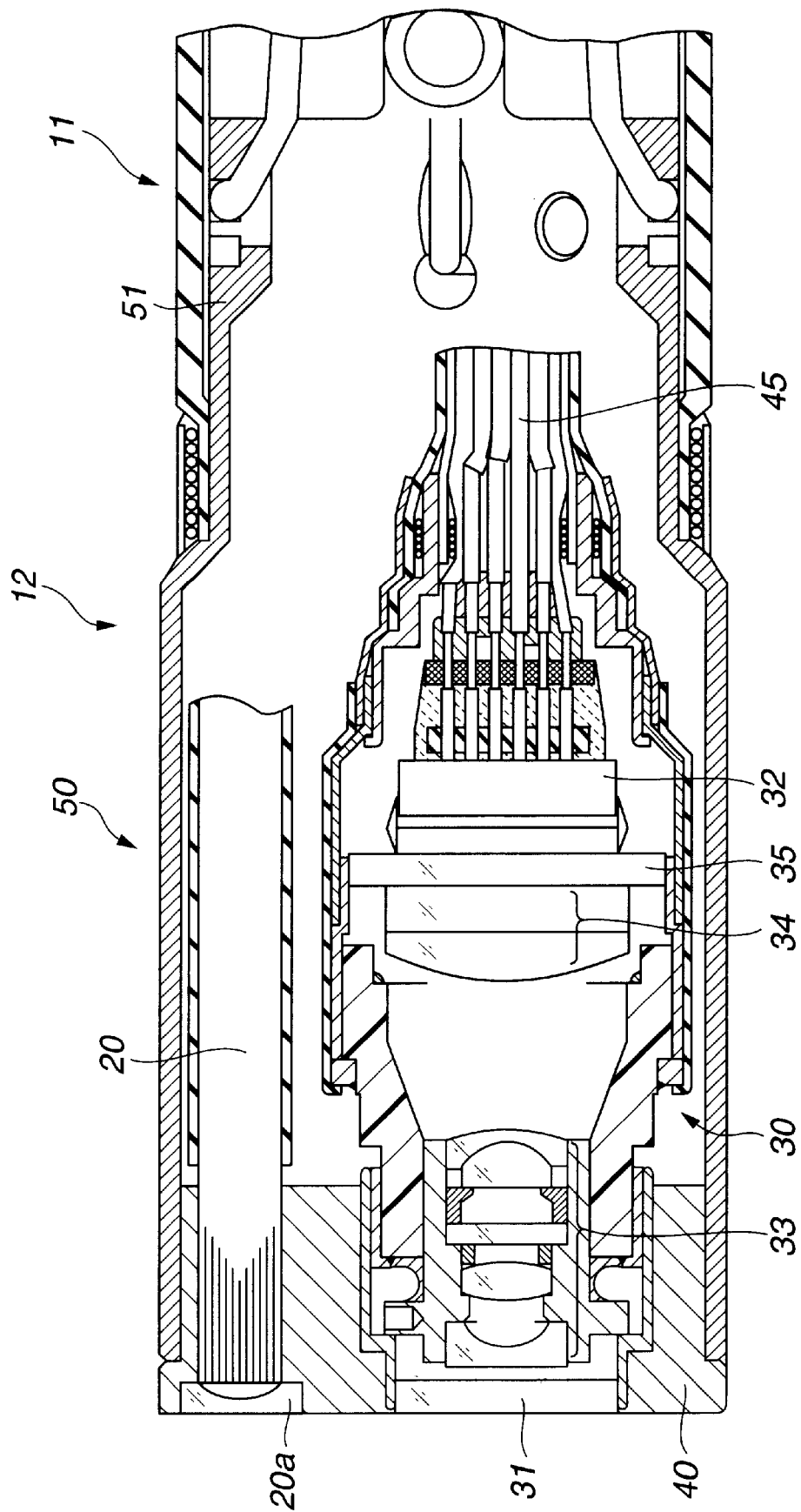
FIG. 2 is a cross-sectional view for describing the tip end portion side of an endoscope insertion section in the first embodiment according to the present invention.
Figure 3:
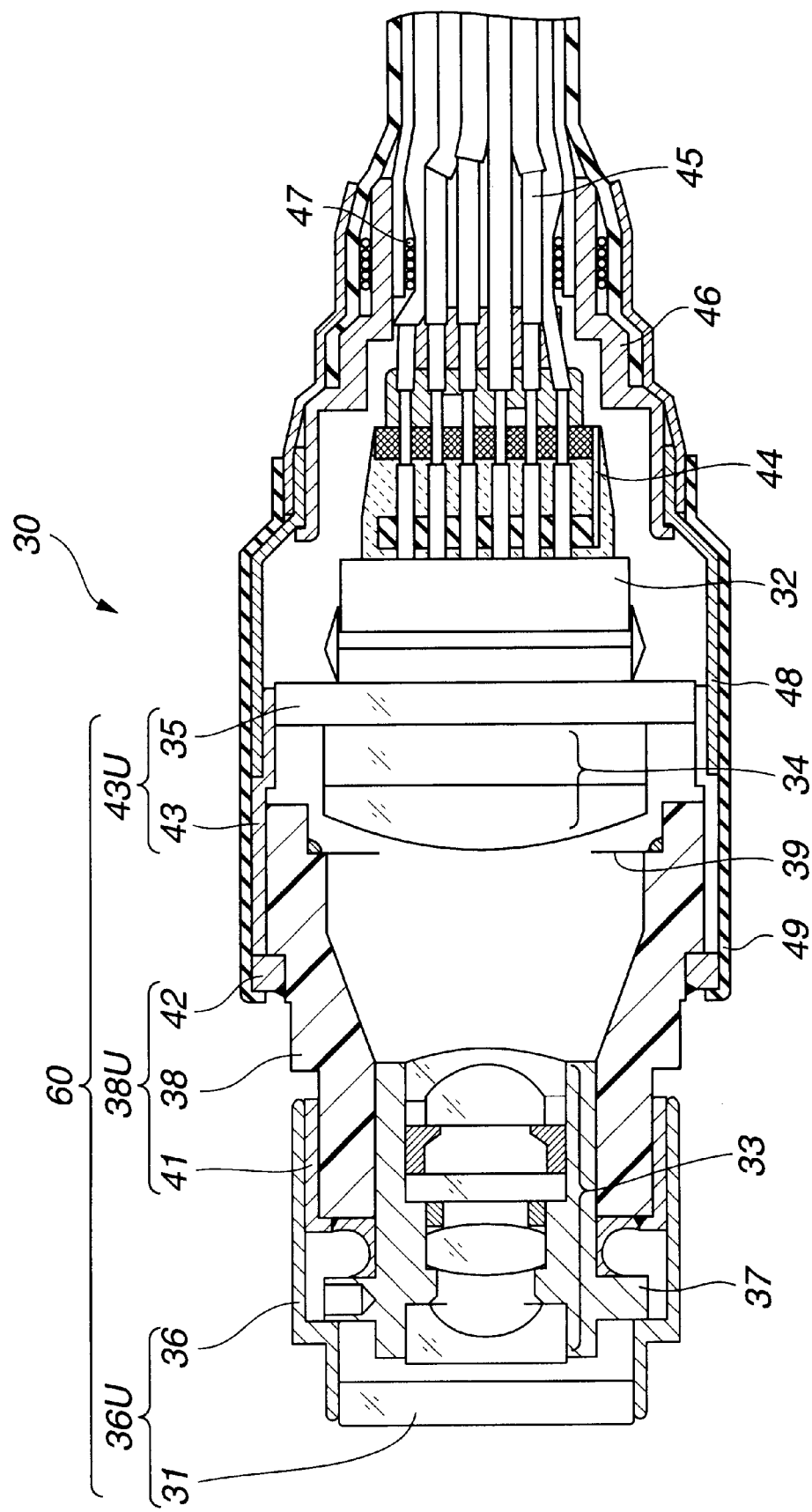
FIG. 3 is a cross-sectional view for describing an image pickup unit shown in FIG. 2.
Figure 4:
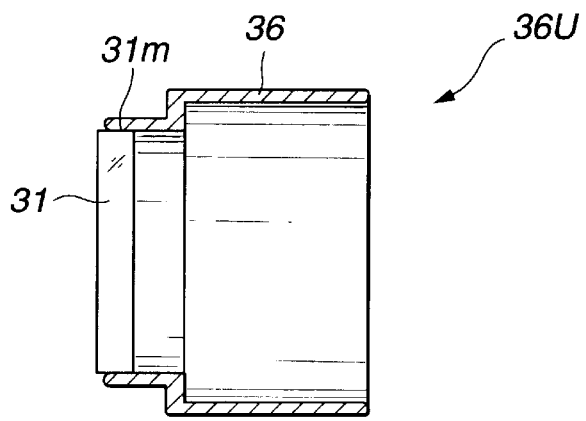
FIG. 4 is an explanatory view for the coupling between a tip end cover glass and a tip end cover glass frame constituting a tip end side unit shown in FIG. 3.
Figure 5:
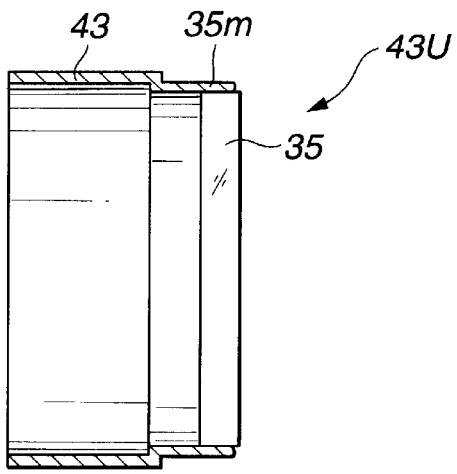
FIG. 5 is an explanatory view for the coupling between a rear end cover glass and a rear end cover glass frame constituting a rear end side unit shown in FIG. 3.
Figure 6:
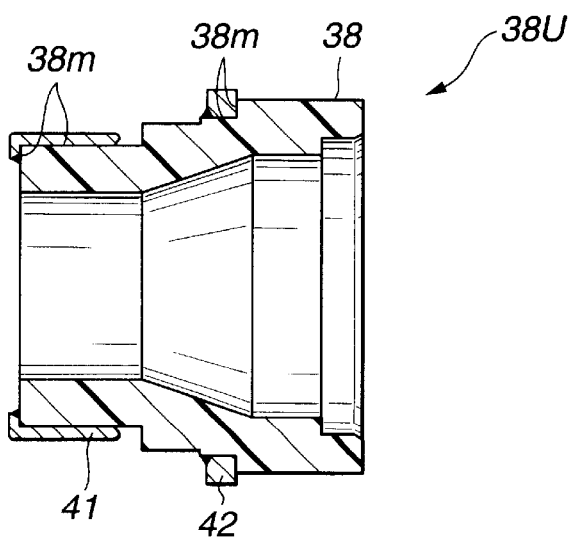
FIG. 6 is an explanatory view for the coupling among an insulating frame, a pipe member and a ring member constituting an insulating unit shown in FIG. 3.
Figure 7:
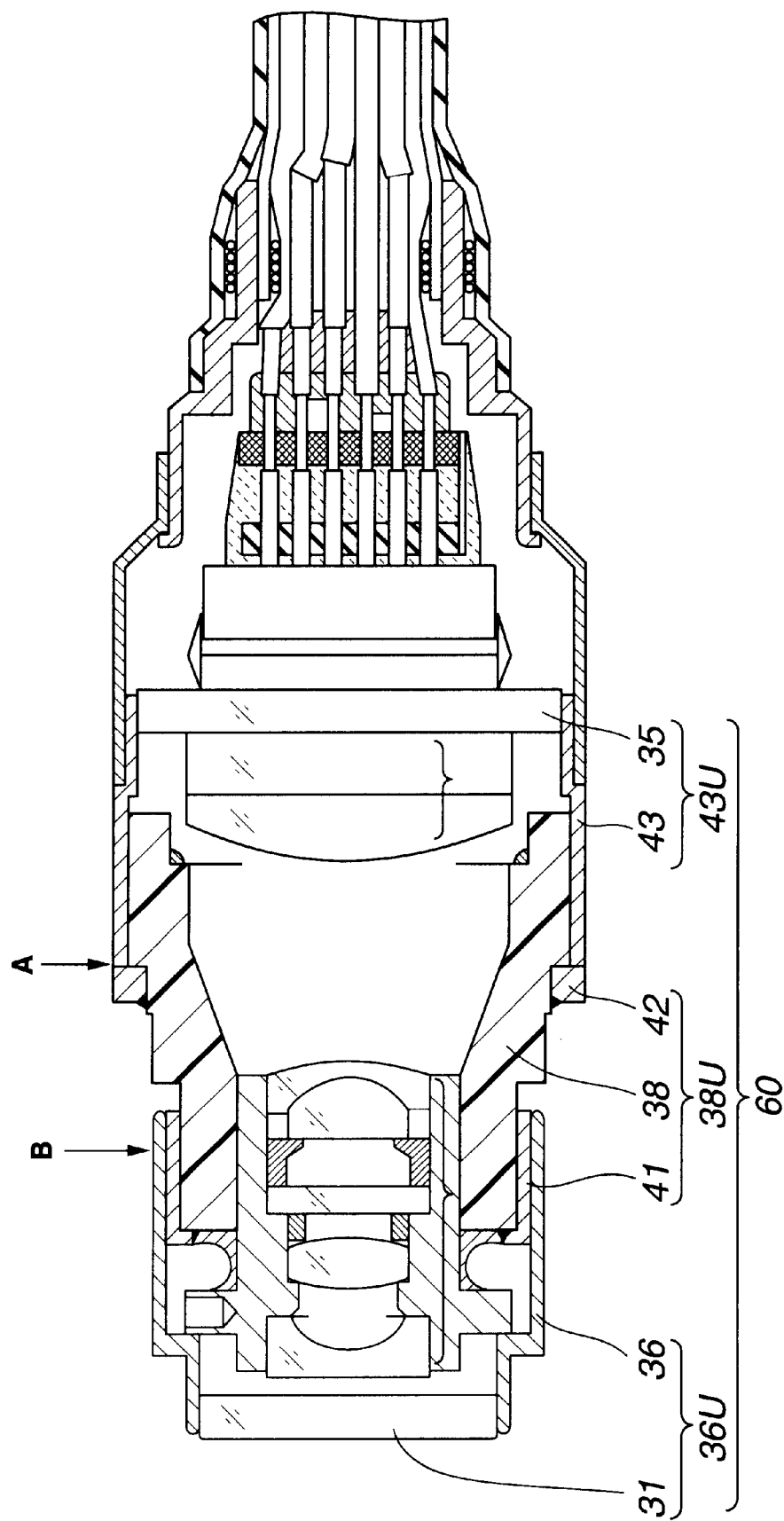
FIG. 7 is an explanatory sectional view for optical system unit assembly procedures.

FIGS. 1 to 7 relate to the first embodiment of the present invention. Specifically, FIG. 1 is an outside view showing an endoscope in the first embodiment according to the present invention. FIG. 2 is a cross-sectional view for describing the tip end portion side of an endoscope insertion section in the first embodiment according to the present invention. FIG. 3 is a cross-sectional view for describing an image pickup unit shown in FIG. 2. FIG. 4 is an explanatory view for the coupling between a tip end cover glass and a tip end cover glass frame constituting a tip end side unit shown in FIG. 3. FIG. 5 is an explanatory view for the coupling between a rear end cover glass and a rear end cover glass frame constituting a rear end side unit shown in FIG. 3. FIG. 6 is an explanatory view for the coupling among an insulating frame, a pipe member and a ring member constituting an insulating unit shown in FIG. 3. FIG. 7 is an explanatory cross-sectional view for optical system unit assembly procedures.

As shown in FIG. 1, an electronic endoscope (to be referred to simply as "endoscope" hereinafter) 1 in the first embodiment according to the present invention mainly consists of an elongate insertion section 2 including an image pickup unit (see FIG. 2), to be described later, having a solid-state image pickup device such as a CCD on a tip end side, an operation section 3 serving as a grip section provided on the rear end portion of the insertion section 2, a universal cord 4 having a proximal portion extending and connected to the rear end portion of the operation section 3, a light guide connector (to be referred to as "LG connector" hereinafter) 5 provided on the rear end portion of the universal cord 4 and connected to a light source unit, which is not shown, a camera cable 6 extending from the side portion of the LG connector 5, and a video connector 7 provided on the tip end portion of the camera cable 6 and connected to a video system center which is not shown. It is noted that a monitor, which is not shown, is connected to the video system center, not shown, connected to the video connector 7. The video system center conducts a signal processing to an image pickup signal obtained by picking up the optical image of a subject region using the solid-state image pickup device, into a standard video signal, and displays the image of the subject region on the monitor.

The insertion section 2 consists of a tip end portion 12 including a bent portion 11 which can be freely bent, and a hard sheath 13 provided continuously to the rear end side of the tip end portion 12.

The operation section 3 is provided with a bending operation lever 3a for freely bending the bent portion 11. This bending operation lever 3a is designed to operate the bent portion 11 so that the portion 11 can be freely bent.

The LG connector 5 is provided with an air supply mouthpiece 14 capable of selecting the state of continuity between the interior and the exterior of the endoscope on a side portion. The air supply mouthpiece 14 can connect a check valve adapter to be described later or a communication adapter detachably.

The camera connector 7 is provided with an electric contact 7a detachably connected to the video system center. A waterproof cap 15 capable of keeping this electric contact 7a watertight is detachably provided to the electric contact 7a of the camera connector 7. Namely, the endoscope 1 is constituted to have a watertight structure preventing water from entering the interior of the endoscope 1.

The tip end portion 12 of the insertion section 2 shown FIG. 2 consists of a light guide 20 serving as an illumination optical system introducing an illumination light for illuminating a subject region in a body cavity and illuminating the subject region from an illumination window 20a, a hard tip end constituting section 40 holding an object lens group 33 fetching the optical image of the subject region illuminated with the illumination light from the light guide 20 from the tip end cove glass 31 and forming an image on the solid-state image pickup device 32 such as a CCD and an image pickup unit 30 continuous to the object lens group 33, picking up a fetched optical image using the solid-state image pickup device 32 through a filter lens group 34 and a rear end cover glass 35 and transferring the image, and a tip end hard section 50 constituting the light guide 20, the image pickup unit 30 and the tip end constituting section 40 watertight and having the first joint 51 serving as the final point joint of the bent portion 11 coupled and fixed to the tip end constituting section 40 by an adhesive agent. The rear end side of the tip end hard section 50 is formed into the bent portion 11 to which a joint group, which is not shown, is continuously provided so as to orient the tip end hard section 50 in an arbitrary direction. Also, though not shown, the tip end portion 12 can be provided with a treatment tool channel for inserting a treatment tool, an air/water supply channel and the like.

The illumination light from the light source, which is not shown, introduced from the light guide fiber 20 illuminates a subject of the subject region from the illumination window 20a of the tip end constituting section 40. The optical image of the subject thus illuminated is fetched from the tip end side cover lens 31 of the tip end constituting section 40 and picked up by the solid-state image pickup device 32 through the object lens group 33, the filter lens group 34 and the rear end cover glass 35, and subjected to photoelectric transfer. A signal derived from the photoelectric transfer by the solid-state image pickup device 32 is processed by the video system center, which is not shown, through a cable 45 and displayed on the monitor.

Next, the detailed structure of the image pickup unit 30 will be described with reference to FIG. 3.

The tip end cover glass 31 formed out of a nonmetal member such as sapphire, on the tip end of the image pickup unit 30 is exposed to the outer surface of the insertion section 2 and assembled with and fixed to a tip end cover glass frame 36 formed out of a metal member, thereby constituting a tip end side unit 36U airtight coupled by soldering or brazing to be describe later. The tip end cover glass frame 36 is coupled to the tip end constituting section 40.

The object lens group 33 is assembled with and fixed to an object lens frame 37 in the rear of the tip end cover glass frame 36. The object lens frame 37 is fixedly bonded to an insulating frame 38 formed out of an insulating material such as ceramic. Ceramic used for the insulating frame 38 is formed out of a material which does not transmit light, and preferably has light shielding and electrical insulating properties, such as black alumina, to prevent light leakage of, for example, an optical fiber flux transmitting the illumination light, which is not shown, from being transmitted into the interior of the insulating frame 38. Black alumina is alumina ceramic containing Ti (titanium), N (nitrogen) and C (carbon).

The rear end of the tip end cover glass frame 36 is fitted into and airtight coupled to the insulating frame 38 by welding to be described later. A stop 39 is fixedly bonded to the insulating frame 38.

A generally cylindrical pipe member 41 formed out of a metal member is fitted into and coupled to the tip end side of the insulating frame 38. On the other hand, a ring-shaped ring member 42 formed of a metal member is fitted into and coupled to the rear end side of the insulating frame 38. An insulating unit 38U is constituted by airtight coupling the pipe member 41 and the ring member 42 to the insulating frame 38 by brazing using soldering to be described later. It is noted that the soldered surface of the insulating frame 38 into which the pipe member 41 and the ring member 42 are fitted and butted is subjected to a surface treatment (metallization) to be described later.

The solid-state image pickup device 32 is positioned relative to and fixedly bonded to the rear end cover glass 35 formed out of a nonmetal member, such as sapphire, by reticule or the like. The filter lens group 34, such as an infrared cut filter, is positioned relative to and fixedly bonded to the rear end cover glass 35.

The rear end cover glass 35 is fitted into a rear end cover glass frame 43 formed out of a metal member, thereby constituting a rear end side unit 43U airtight brazed by soldering to be described later. Further, the proximal end of the rear end cover glass frame 43 is fitted into and airtight brazed to the insulating frame 38 by welding to be described later.

The solid-state image pickup device 32 is electrically connected to the cable 45 through a substrate 44 by soldering or the like. Electronic components such as IC's and capacitors are incorporated into the substrate 44 and sealed by an insulating sealant.

The cable 45 is inserted into a cable stopper member 46 formed out of a metal member and fixed by a bobbin fixing portion 47 fixedly winding a thread or a wire around the cable 45 through a notch portion, which is not shown, of the cable stopper member 46. The interior of the cable stopper member 46 is filled with an adhesive agent having low steam permeability, thereby providing a structure which makes it difficult for steam to enter the interior of the image pickup unit 30 provided with the solid-state image pickup device 32 from between the cable 45 and the cable stopper member 46.

A shield frame 48 is airtight assembled with the rear end cover glass frame 43 by welding outside of the solid-state image pickup device 32. The shield frame 48 and the cable stopper member 46 are airtight assembled with each other by welding.

Further, the insulating frame 38, the rear end cover glass frame 43 and the shield frame 48 are covered with a heat-shrinkable tube 49 made of PET (polyethylene terephthalate) or the like having a high shrinkage rate.

In this embodiment, the tip end side unit 36U and the rear end side unit 43U are constituted by subjecting the nonmetal members such as the tip end cover glass 31 and the rear end cover glass 35 to a surface treatment (metallization) and airtight brazing the surface-treated portions of these nonmetal members to the metal members such as the tip end cover glass frame 36 and the rear end cover glass frame 43 by soldering, respectively. Further, an optical system unit 60 is constituted by airtight coupling the metal member of the tip end side unit 36U and the rear end side unit 43U to the metal member of the insulating unit 38U in which the pipe member 41, the ring member 42 are airtight coupled to the insulating frame 38, by welding.

First, with reference to FIG. 4, description will be given to the coupling between the tip end cover glass 31 and the tip end cover glass frame 36 which constitute the tip end side unit 36U.

As shown in FIG. 4, the tip end cover glass 31 is designed to be airtight assembled with the tip end cover glass frame 36. The outer peripheral surface of this tip end cover glass 31, on which surface the tip end cover glass 31 is fitted into the tip end cover glass frame 36, is subjected to a surface treatment (metallization) 31m. While the tip end cover glass 31 is formed out of sapphire in this embodiment, it may be formed out of glass if it has high heat resistance and high-temperature steam resistance. First, the surface treatment will be described hereinafter.

In the surface treatment of the tip end cover glass 31, a Cr (chromium) film having high adhesion to sapphire and glass is formed on the lowest layer (metallized layer). The Cr (chromium) layer is formed by deposition under vacuum or sputtering under vacuum under which the layer has high adhesion. An Ni (nickel) layer is formed, as an outermost layer, by deposition under vacuum, sputtering under vacuum or plating. Alternatively, a mixture of Mo (molybdenum) and Mn (manganese) may be baked and then Ni (nickel) and Au (gold) are plated on the resultant layer. In the latter case, higher heat resistance can be obtained.

At least an inner surface portion of the surface of the tip end cover glass frame 36, into which portion the tip end cover glass 31 is fitted, is electroplated with Ni (nickel).

Using a positioning jig, which is not shown, the tip end cover glass 31 is positioned relative to the tip end glass frame 36 and fixedly soldered to the frame 36, thereby constituting the tip end side unit 36U. If a flux is used when soldering, the flux is washed away.

Next, description will be given to the coupling between the rear end cover glass 35 and the rear end cover glass frame 43 which constitute the rear end side unit 43U with reference to FIG. 5.

As shown in FIG. 5, the rear end cover glass 35 is designed to be airtight assembled with the rear end cover glass frame 43. The outer peripheral surface of this rear end cover glass 35, on which surface the rear end cover glass 35 is fitted into the rear end cover glass frame 43, is subjected to a surface treatment (metallization) 35m in the same manner as that described with reference to FIG. 4. Likewise, using a positioning jig, which is not shown, the rear end cover glass 35 is positioned relative to the rear end cover glass frame 43 and fixedly soldered to the frame 43, thereby constituting the rear end side unit 43U. If a flux is used when soldering, the flux is washed away.

Next, description will be given to the coupling among the insulating frame 38, the pipe member 41 and the ring member 42 which constitute the insulating unit 38U with reference to FIG. 6.

The surface of the pipe member 41 is electroplated with Ni (nickel) and the surface of the ring member 42 is electroplated with Ni (nickel), as well.

The soldered surface of the insulating frame 38, into which the pipe member 41 and the ring member 42 are fitted and butted, is subjected to a surface treatment (metallization) 38m. In this surface treatment (metalization), Cr (chromium) and Ni (nickel) films are formed from below. These films are formed by vacuum deposition or sputtering. Alternatively, a mixture of Mo (molybdenum) and Mn (manganese) may be baked and Ni (nickel) may be plated on the resultant layer. In the latter case, higher heat resistance is obtained. It is noted that the surface treatment is not conducted to the insulating frame 38 except for the soldered surface.

The insulating unit 38U is constituted by airtight coupling the pipe member 41 and the ring member 42 to the insulating frame 38 which has been subjected to the surface treatment stated above by soldering. If a flux is used when soldering, the flux is washed away. As a result, the pipe member 41 and the ring member 42 can be electrically insulated.

As stated above, the tip end side unit 36U airtight constituted out of the tip end cover glass 31 and the tip end cover glass frame 36, the rear end side unit 43U airtight constituted out of the rear end cover glass 35 and the rear end cover glass frame 43, and the insulating unit 38U constituted out of the insulating frame 38, the pipe member 41 and the ring member 42 are airtight coupled to one another by welding, thereby constituting the optical system unit 60.

Now, procedures for assembling the optical system unit 60 will be described with reference to FIG. 7.

As shown in FIG. 7, the solid-state image pickup device 32 and the filter lens group 34 are assembled with the rear end side unit 43U airtight constituted out of the rear end cover glass 35 and the rear end cover glass frame 43. Thereafter, the insulating unit 38U constituted out of the insulating frame 38, the pipe member 41 and the ring member 42 is assembled with the resultant structure, and an all-round laser beam is applied from an arrow A direction. The arrow A direction is a butt portion between the tip end portion of the rear end cover glass frame 43 and the ring member 42. By applying the all-round laser beam to the butt portion, it is possible to airtight weld the ring member 42 and the cover glass frame 43 (butt welding).

Next, the object lens frame 37 with which the object lens group 33 is assembled is assembled with the insulating unit 38U constituted out of the insulating frame 38, the pipe member 41 and the ring member 42, the distance between the object lens group 43 and the solid-state image pickup device 32 is adjusted to thereby take the focus. Thereafter, the object lens frame 37 is fixedly bonded to the insulating unit 38U.

The tip end side unit 36U airtight constituted out of the tip end cover glass 31 and the tip end cover glass frame 36 is fitted into the insulating unit 38U consisting of the insulating frame 38, the pipe member 41 and the ring member 42 from externally and an all-round laser beam is applied from an arrow B direction. This arrow B direction is a portion at which the tip end cover glass frame 36 is fitted into the pipe member 41 from externally. By applying the all-round laser beam to the portion, heat generated by the laser penetrates the tip end cover glass frame 36 and melts the pipe member 41, thereby making it possible to airtight weld the tip end cover glass frame 36 to the pipe member 41 (penetration welding).

As for the laser used herein, a pulse wave YAG laser beam capable of fine-adjusting laser output is effective since it is necessary to make metal components at the welded portions thin if the image pickup unit 30 is small in size. Further, for the purpose of ensuring airtightness, it is necessary for the laser beam to allow a sufficient pulse overlap quantity. In addition, since airtight coupling after the electronic components are assembled with the optical system unit 60 which is an airtight unit, is conducted by welding, washing operation is not necessary and heat has no adverse effect on the electronic components.

By the above-stated assemble, the optical system unit 60 can be constituted. Accordingly, the image pickup unit 30 can be constituted.

An endoscope test is performed using the endoscope 1 having the image pickup unit 30 constituted as stated above and autoclave sterilization is conducted after the completion of the test. Namely, the endoscope 1 is placed into the chamber (treatment chamber) of an autoclave sterilization apparatus. In a sterilization pretreatment step, the interior of the chamber is evacuated. In a sterilization step, the chamber is filled with high-temperature, high-pressure steam, which steam also enters the interior of the endoscope 1 to increase humidity. In a dry step, the interior of the chamber is vacuum and the interior of the endoscope is somewhat dried but not completely. A space in which the object lens group 33 exists is airtight blocked by the airtight coupled optical system unit 60 through which no steam transmits, so that steam does not at all enter the space.

Further, if the endoscope 1 is used right after the completion of the autoclave sterilization, sterilized water is often sprayed onto the endoscope 1 to quickly cool down the endoscope 1. In this case, since the outer surface of the endoscope 1 is quickly cooled down, the tip end cover glass 31 exposed to the outer surface is cooled down quickly as well. However, since gas within the tip end cover glass 31 does not contain steam, dew is not formed in the glass 31 (the glass 31 is not clouded up with steam).

With the above-stated constitution, the endoscope 1 in this embodiment has the following advantages:

(1) The optical components such as object lens group 43, the tip end cover glass 31 and the rear end cover glass 35 are not deteriorated by the autoclave sterilization (high-temperature, high-pressure steam sterilization) and are not clouded up with dew formed by the entry of steam, so that autoclave sterilization can be conducted repeatedly.
(2) Even if the endoscope 1 is quickly cooled down after the autoclave sterilization, no dew is formed in the tip end cover glass 31 (or the tip end cover glass 31 is not clouded up with dew).
(3) since the distance between the object lens group 43 and the solid-state image pickup device 32 can be easily adjusted (the focus can be easily taken), it is possible to observe a subject region using a clear image.
(4) Since the outside diameter of the periphery of the lens of the image pickup unit 30 can be suppressed to be small, it is possible to reduce the outside diameter of the insertion section 2 and to thereby ease the burden of a patient.

[Second Embodiment]

Figure 8:
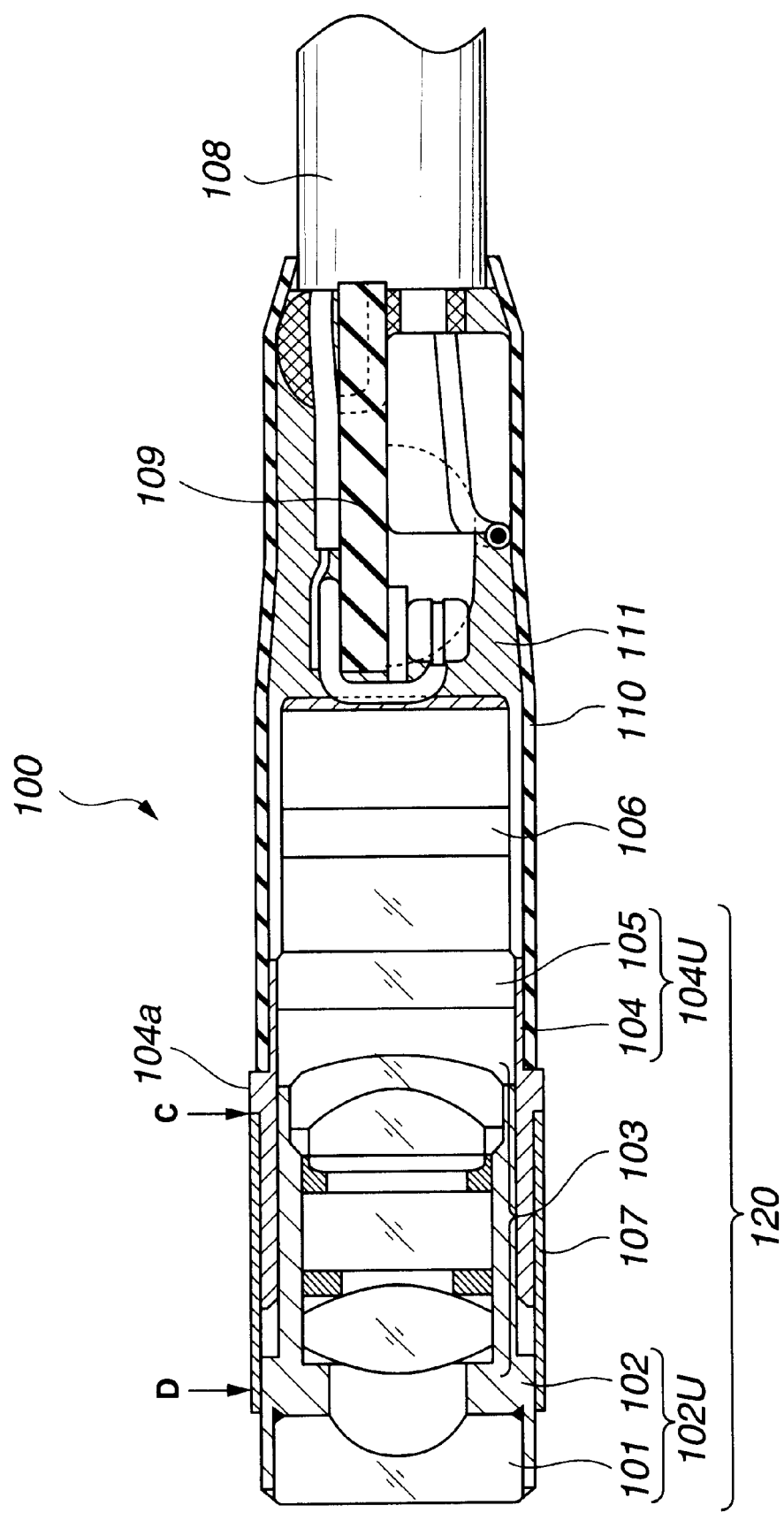
FIG. 8 is a cross-sectional view for describing an image pickup unit in the second embodiment according to the present invention.

FIG. 8 is a cross-sectional view for describing an image pickup unit in the second embodiment according to the present invention.

As shown in FIG. 8, in an image pickup unit 100 in the second embodiment, a tip end lens 101 is exposed to a tip end side and airtight assembled with and fixed to an object lens frame 102 formed out of a metal member, thereby constituting a tip end side unit 102U airtight brazed by soldering in the same manner as that described with reference to FIG. 4. Also, an object lens group 103 is assembled with the object lens frame 102. The outer peripheral surface of the tip end lens 101, on which surface the tip end lens 101 is fitted into the object lens frame 102, is subjected to a surface treatment (metallization) as in the case of the first embodiment described above.

A cover glass 105 is airtight assembled with and fixed to a cover glass frame 104 formed out of a metal member, thereby constituting a rear end side unit 104U airtight brazed by soldering in the same manner as that described with reference to FIG. 5. The outer peripheral surface of the cover glass 105, on which surface the cover glass 105 is fitted into the cover glass frame 104, is subjected to a surface treatment (metallization) as in the case of the first embodiment described above.

The optical axis of the solid-state image pickup device 106 is adjusted by reticule or the like and the solid-state pickup device 106 is fixed to the cover glass 105 by plane-bonding. This solid-state image pickup device 106 incorporates a substrate 109 onto which electronic components such as IC's and capacitors are mounted, and is sealed by an insulating adhesive agent. The solid-state image pickup device 106 or the substrate 109 is electrically connected to a cable 108. The cable 108 is connected to a terminal at a connector section, which is not shown, to be thereby connected to a video system center or the like which is not shown.

A butt portion 104a is provided on the outer peripheral surface of the cover glass frame 104. A pipe member 107 is to be butted against the butt portion 104a. This pipe member 107 includes at least the end portion of the cover glass frame 104 and covers the exterior of the object lens frame 102 and that of the cover glass frame 104.

A portion from the rear end-side outer peripheral portion of the cover glass frame 104 to the tip end-side end portion of the cable 108 is covered with a heat-shrinkable tube 110, such as PET (polyethylene phthalate), having a high shrinkage rate and the interior of the heat-shrinkable tube 110 is filled with, for example, an epoxy based adhesive agent 111.

In the second embodiment, the rear end side unit 104U airtight constituted out of the cover glass 105 and the cover glass frame 104 is fitted into and assembled with the tip end side unit 102U airtight constituted out of the tip end lens 101 and the object lens frame 102 from externally. The pipe member 107 is butted against the butt portion 104a provided on the outer peripheral surface of the cover glass frame 104, and covers the exterior of the object lens frame 102 and that of the cover glass frame 104 and these metal members are airtight coupled with one another by welding, thereby constituting the optical system unit 120.

Next, procedures for assembling the optical system unit 120 will be described.

An object lens group 103 is assembled with the tip end side unit 102U airtight constituted by soldering the tip end lens 101 to the object lens frame 102. Then, the solid-state image pickup device 106 is bonded to the cover glass 105 of the rear end side unit 104U airtight constituted by soldering the cover glass 105 to the cover glass frame 104, and the substrate 109 and the like are incorporated into the solid-state image pickup device 106. The cover glass frame 104 is fitted into the object lens frame 102 from externally and moved in an optical axis direction to thereby adjust the focusing between the object lens group 103 and the solid-state image pickup device 106, and the object lens frame 102 and the cover glass frame 104 are fixedly bonded to each other.

Next, the pipe member 107 is covered on the object lens frame 102 and the cover glass frame 104 and inserted into the butt portion 104a of the cover glass frame 104.

A butt portion (arrow C) between the pipe member 107 and the butt portion 104a of the cover glass frame 104 is applied with an all-round laser beam and welded. Further, a fitted portion (arrow D) between the object lens frame 102 and the pipe member 107 is applied with an all-round laser beam and welded.

By the above-stated assembly process, the optical system unit 120 can be constituted. Accordingly, the image pickup unit 100 can be constituted.

The endoscope having the image pickup unit 100 constituted as stated above is placed into the chamber (treatment chamber) of an autoclave sterilization apparatus, which is not shown, and subjected to autoclave sterilization. Since a space in which the object lens group 103 exists is airtight blocked by the airtight coupled optical system unit 120 into which steam does not transmit, steam does not at all enter the space.

With the above-stated constitution, the endoscope in this embodiment employs the tip end lens 101 without using the tip end cover glass. Due to this, compared with the endoscope 1 in the first embodiment, the outside diameter of the tip end of the insertion section does not increase even if an optical system having a wide angle of view is employed. Further, since the image pickup unit 100 is welded and fixed after adjusting the angle of view and focusing, it is possible to keep the interior of the optical system unit 120 airtight without increasing the outside diameter of the image pickup unit 100.

In the first and second embodiments, description has been given while using the soft endoscope having the bent portion 11 at the endoscope insertion section 2. The present invention should not be limited to these embodiments and can be applied to various apparatuses having an optical system such as a hard endoscope and a camera provided externally with an endoscope.

It is evident that different embodiments can be constituted based on the invention in a wide range without departing from the spirit and scope of the invention. The present invention should not be restricted by the specific embodiments except that the invention is limited by claims which follows.

What is claimed is:

1. An endoscope comprising:
    a plurality of units formed by airtight coupling metal members to at least partially metallized portions of surfaces of nonmetal members by one of soldering and brazing, respectively; and
    an optical system unit integrally formed by airtight welding said metal members of said plurality of units.

2. An endoscope according to claim 1, wherein
    said optical system unit includes a tip end side unit arranged at a tip end side of a tip end portion of an insertion section of said endoscope, a rear end side unit arranged at a rear end side of the tip end portion of the insertion section of said endoscope, and an insulating unit provided between said tip end side unit and said rear end side unit, said optical system unit constituted by airtight coupling the metal members of the tip end side unit, the rear end side unit and the insulating unit by welding.

3. An endoscope according to claim 2, wherein
    said tip end side unit is formed by airtight coupling a tip end cover glass arranged at the tip end side of the tip end portion of the insertion section of said endoscope to a metallized portion between the tip end cover glass and a tip end cover glass frame assembled with the tip end cover glass by one of the soldering and the brazing;
    said rear end side unit is formed by airtight coupling a rear end cover glass arranged at the rear end side of the tip end portion of the insertion section of said endoscope to a metallized portion between the rear end cover glass and a rear end cover glass frame assembled with the rear end cover glass by one of the soldering and the brazing;
    said insulating unit is formed by airtight coupling at least partially metallized portions of surfaces of both ends of an insulating frame which can be arranged between said tip end cover glass frame of said tip end side unit and said rear end cover glass frame of said rear end side unit to two metal members provided on the both ends of said insulating frame by one of the soldering and the brazing; and
    said optical system unit is formed by airtight coupling said tip end cover glass frame of said tip end side unit to the metal member of said insulating unit and the metal member of said insulating unit to said rear end cover glass frame of said rear end side unit by welding.

4. An endoscope according to claim 2, wherein
    at least an outer peripheral portion of said tip end cover glass is metallized, the outer peripheral portion fitted into said tip end cover glass frame; and
    at least an outer peripheral portion of said rear end cover glass is metallized, the outer peripheral portion is fitted into said rear end cover glass frame.

5. An endoscope according to claim 2, wherein
    at least a portion of said tip end cover glass frame is metallized, said tip end cover glass fitted into the portion; and
    at least a portion of said rear end cover glass frame is metallized, said rear end cover glass fitted into the portion.

6. An endoscope according to claim 2, wherein
    said optical system unit constitutes an image pickup unit by fixedly bonding a solid-state image pickup device to said rear end cover glass.

7. An endoscope according to claim 6, wherein
    said optical system unit has an object lens group for forming an optical image fetched from said tip end cover glass onto said solid-state image pickup unit, and an object lens frame for assembling and fixing said object lens group, said object lens frame fixedly bonded to said insulating frame.

8. An endoscope according to claim 6, wherein
    said image pickup unit has a shield cylinder arranged near said solid-state image pickup device and airtight assembled with said rear end cover glass frame by welding, and a cable stopper member armoring a cable electrically connected to said solid-state image pickup device directly or through electronic components; and
    said image pickup unit is constituted by airtight assembling the cable stopper member with the shield cylinder by welding.

9. An endoscope according to claim 8, wherein
    said image pickup unit is constituted to be capable of assembling said shield cylinder after assembling said solid-state image pickup device, said cable and said cable stopper member.

10. An endoscope according to claim 8, wherein
    said insulating frame, said rear end cover glass and said shield cylinder are covered with a heat-shrinkable tube having a high shrinkage rate.

11. An endoscope according to claim 1, wherein said welding is laser welding for applying an all-round laser beam onto outer peripheries of said metal members.

12. An endoscope according to claim 2, wherein said insulating frame is formed out of a light shielding member.

13. An endoscope according to claim 1, wherein said optical system unit has a tip end side unit arranged at a tip end side of a tip end portion of an insertion section of said endoscope, a rear end side unit arranged at a rear end side of the tip end portion of the insertion section of said endoscope, and a cylindrical member made of metal and provided between said tip end side unit and said rear end side unit, said optical system unit constituted by airtight coupling the metal members of the tip end side unit, the rear end side unit and the cylindrical member with one another by welding.

14. An endoscope according to claim 13, wherein said tip end side unit is formed by airtight coupling a tip end lens arranged at the tip end side of the tip end portion of the insertion section of said endoscope to a metallized portion between the tip end lens and a tip end lens frame assembled with the tip end lens by one of soldering and brazing;

said rear end side unit is formed by airtight coupling a cover glass arranged at the rear end side of the tip end portion of the insertion section of said endoscope to a metallized portion between the cover glass and a cover glass frame assembled with the cover glass by one of the soldering and the brazing;

said cylindrical member is butted against a butt portion provided on an outer peripheral surface of said cover glass frame, includes at least an end portion of said cover glass frame, and covers exteriors of said tip end lens frame and said cover glass frame; and said optical system unit is constituted by airtight coupling said tip end lens frame of said tip end side unit to said cylindrical member and said cylindrical member to said cover glass frame of said rear end side unit by welding.

15. An endoscope according to claim 14, wherein said optical system unit is constituted by airtight coupling said cylindrical member to a butt portion between said cylindrical member and the butt portion of said cover glass frame by welding, and by airtight coupling said tip end lens frame to a fitted portion between said tip end lens frame and said cylindrical member by welding.

16. An endoscope according to claim 13, wherein at least an outer peripheral portion of said tip end lens is metallized, the outer peripheral portion fitted into said tip end lens frame; and at least an outer peripheral portion of said cover glass is metallized, the outer peripheral portion fitted into said cover glass frame.

17. An endoscope according to claim 13, wherein at least a portion of said tip end lens frame is metallized, said tip end lens fitted into said tip end lens frame; and at least a portion of said cover glass frame is metallized, said cover glass fitted into said cover glass frame.

18. An endoscope according to claim 13, wherein said optical system unit constitutes an image pickup unit by fixedly bonding a solid-state image pickup device to said cover glass.

19. An endoscope according to claim 18, wherein said optical system unit has an object lens group forming an optical image fetched from said tip end lens onto said solid-state image pickup device; and said tip end side unit is constituted by arranging said object lens group on said tip end lens frame.

20. An endoscope according to claim 13, wherein said welding is laser welding for applying an all-round laser beam onto an outer periphery of said cylindrical member.

21. An endoscope according to claim 1, wherein said endoscope includes:
  a first unit formed by airtight coupling a first metal frame to an at least partially metallized portion of a surface of a first nonmetal member by one of soldering and brazing; and
  a second unit formed by airtight coupling a second metal frame to an at least partially metallized portion of a surface of a second nonmetal member by one of soldering and brazing, and said optical system unit is constituted by arranging a third metal frame between said first metal frame of said first unit and said second metal frame of said second unit, and by airtight coupling said first metal frame to said third metal frame and said third metal frame to said second metal frame by welding.

22. An endoscope according to claim 21, wherein said first unit is a tip end side unit formed by airtight coupling a tip end lens which is the first nonmetal member to a metallized portion between the tip end lens and a tip end lens frame which is the first metal frame assembled with the tip end lens by one of soldering and brazing;

said second unit is a rear end side unit formed by airtight coupling a cover glass which is the second nonmetal member to a metallized portion between the cover glass and a cover glass frame which is the second metal frame assembled with the cover glass by one of the soldering and the brazing;

said third metal frame is a cylindrical member butted against a butt portion provided on an outer peripheral surface of said cover glass frame, including at least an end portion of said cover glass frame, and armoring an exterior of said tip end lens frame and an exterior of said cover glass frame; and said optical system unit is constituted by airtight coupling said tip end lens frame of said tip end side unit to said cylindrical member and said cylindrical member to said cover glass frame of said rear end side unit by welding.

23. An endoscope according to claim 1, wherein said endoscope includes:
  a first unit formed by airtight coupling a first metal frame to an at least metallized portion of a surface of a first nonmetal member by one of soldering and brazing;
  a second unit formed by airtight coupling a second metal frame to an at least partially metallized portion of a surface of a second nonmetal member by one of soldering and brazing, and
  an insulating unit formed by airtight coupling at least partially metallized portions of surface on both ends of an insulating frame which can be arranged between said first metal frame of said first unit and said second metal frame of said second unit to two metal members provided on the both ends of said insulating frame by one of the soldering and the brazing, and said optical system unit is constituted by arranging said insulating unit between said first metal frame of said first unit and said second metal frame of said second unit, and by airtight coupling said first metal frame to the metal member of said insulating frame and said second metal frame to the metal member of said insulating unit by welding.

24. An endoscope according to claim 23, wherein said first unit is a tip end side unit formed by airtight coupling a tip end cover glass which is the first nonmetal member to a metallized portion between the tip end cover glass and a tip end cover glass frame which is the first metal frame assembled with the tip end cover glass by one of the soldering and the brazing;

said second unit is a rear end side unit formed by airtight coupling a rear end cover glass which is the second nonmetal member to a metallized portion between the rear end cover glass and a rear end cover glass frame which is the second metal frame assembled with the rear end cover glass by one of the soldering and the brazing;

said insulating unit is formed by airtight coupling at least partially metallized portions on surfaces of both ends of an insulating frame which can be arranged between said tip end cover glass frame of said tip end side unit and said rear end side cover glass frame of said rear end side unit to two metal members provided on the both ends of said insulating frame by one of the soldering and the brazing; and said optical system unit is constituted by airtight coupling said tip end cover glass frame of said tip end side unit to the metal member of said insulating unit and the metal member of said insulating unit to said rear end cover glass frame of said rear end side unit by welding.

* * * * *